United States Patent
Rao et al.

(10) Patent No.: US 10,653,395 B2
(45) Date of Patent: May 19, 2020

(54) TRANSMIT POWER BASED ON HARMONIC TO FUNDAMENTAL RELATIONSHIP IN MEDICAL ULTRASOUND IMAGING

(71) Applicant: Siemens Medical Solutions USA, Inc., Malvern, PA (US)

(72) Inventors: Bimba Rao, San Jose, CA (US); Sharleen Marshall, San Ramon, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 752 days.

(21) Appl. No.: 14/627,705

(22) Filed: Feb. 20, 2015

(65) Prior Publication Data
US 2016/0242746 A1    Aug. 25, 2016

(51) Int. Cl.
*A61B 8/00* (2006.01)
*A61B 6/00* (2006.01)
*A61B 8/14* (2006.01)
*A61B 8/08* (2006.01)

(52) U.S. Cl.
CPC .......... *A61B 8/54* (2013.01); *A61B 6/56* (2013.01); *A61B 8/14* (2013.01); *A61B 8/52* (2013.01)

(58) Field of Classification Search
None
See application file for complete search history.

(56) References Cited

U.S. PATENT DOCUMENTS

| | | | |
|---|---|---|---|
| 6,544,177 B1 * | 4/2003 | Robinson | A61B 8/481 600/443 |
| 6,858,008 B2 | 2/2005 | Li et al. | |
| 6,899,681 B1 * | 5/2005 | Phillips | G01S 7/52026 600/437 |
| 8,043,219 B2 | 10/2011 | Chomas | |
| 8,357,094 B2 | 1/2013 | Mo et al. | |
| 2003/0158479 A1 | 8/2003 | Li et al. | |
| 2006/0064018 A1 * | 3/2006 | Chomas | A61B 8/481 600/459 |
| 2007/0073146 A1 | 3/2007 | Phillips et al. | |
| 2010/0094125 A1 * | 4/2010 | Younge | A61B 8/12 600/424 |
| 2014/0187946 A1 * | 7/2014 | Miller | A61B 8/5207 600/440 |
| 2014/0243667 A1 * | 8/2014 | Wilkening | A61N 7/00 600/438 |
| 2015/0297173 A1 * | 10/2015 | Klock | G01S 15/899 600/442 |

OTHER PUBLICATIONS

PCT Search Report and Written Opinion from counterpart international application No. PCT/IB2016/050791, filed Feb. 15, 2016, 12 pages total.

* cited by examiner

*Primary Examiner* — Katherine L Fernandez

(57) ABSTRACT

Transmit power is adaptively set in medical diagnostic ultrasound imaging. The relative strength, such as a ratio, of harmonic and fundamental responses is calculated. This relative strength is used to set the transmit power. The transmit power may be set following ALARA while providing enough information for harmonic imaging.

14 Claims, 1 Drawing Sheet

US 10,653,395 B2

TRANSMIT POWER BASED ON HARMONIC TO FUNDAMENTAL RELATIONSHIP IN MEDICAL ULTRASOUND IMAGING

BACKGROUND

The present embodiments relate to medical diagnostic ultrasonic imaging, and in particular, to systems that adapt acoustic output power.

In some ultrasound imaging, the transmit power is to be set as low as possible to ensure patient safety, such as for implementing the Food and Drug Administration's (FDA's) as low as reasonably achievable (ALARA) principle. For example, fetal imaging and TEE imaging (especially pediatric) use ALARA.

Fetal imaging often uses harmonic imaging modes. Since the image quality of a harmonic image may vary significantly with patient body type, the ideal transmit power setting may not be pre-determined in the factory. The user manually adjusts the transmit power on each and every patient until image quality is just acceptable. Adjusting transmit power on each patient to find the ideal value is time consuming and hinders workflow.

Transmit power automation has been used in other settings. Signal-to-noise ratios are used to automatically determine transmit power. Even with good signal-to-noise ratio, the harmonic image quality may be significantly degraded if the fundamental signal leakage into the harmonic information is strong.

SUMMARY

By way of introduction, the preferred embodiments described below include methods, systems, instructions, and computer readable media for setting transmit power in medical diagnostic ultrasound imaging. The relative strength, such as a ratio, of harmonic and fundamental responses is calculated. This relative strength is used to adaptively and automatically set the transmit power. The transmit power may be set following ALARA while providing enough information for harmonic imaging.

In a first aspect, a method is provided for setting transmit power in medical diagnostic ultrasound imaging. An ultrasound scanner measures a fundamental response and a harmonic response at a location in a patient. A ratio of the fundamental and harmonic responses is calculated. A transmit power of a transmitter of the ultrasound scanner is set as a function of the ratio of the fundamental and harmonic responses. The ultrasound scanner images the patient using the transmit power.

In a second aspect, a medical diagnostic imaging system is provided for setting transmit power. A transducer is operable to transmit acoustic energy and receive responses to the acoustic energy. A transmit beamformer is configured to cause the transducer to transmit the acoustic energy. A receive beamformer is configured to beamform a signal from the responses to the acoustic energy. A processor is configured to determine a relationship between fundamental and harmonic levels of the signal and to set a power of subsequent transmission of acoustic energy as a function of the relationship.

In a third aspect, a non-transitory computer readable storage medium has stored therein data representing instructions executable by a programmed processor for setting transmit power in medical diagnostic ultrasound imaging. The storage medium includes instructions for calculating a value as a function of harmonic and fundamental information, determining the transmit power for an imaging condition of an ultrasound imager as a function of the value, and configuring the ultrasound imager to use the transmit power for the imaging condition.

The present invention is defined by the following claims, and nothing in this section should be taken as a limitation on those claims. Further aspects and advantages of the invention are discussed below in conjunction with the preferred embodiments and may be later claimed independently or in combination.

DETAILED DESCRIPTION OF THE PRESENTLY PREFERRED EMBODIMENTS

Ultrasound transmit power is automatically set based on relative harmonic and fundamental responses, such as on a harmonic-to-fundamental ratio. The harmonic-to-fundamental ratio or other measure of relative strength is used to determine a transmit power for a given imaging condition. The transmit power is automatically set to provide the best image quality for each patient while maintaining lower or ALARA power.

Figure 1:
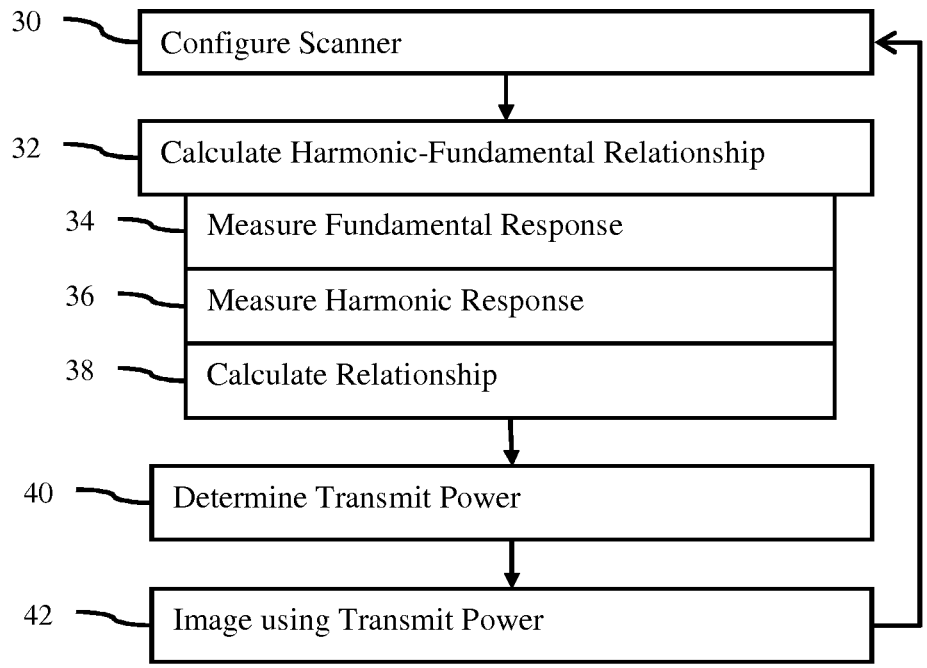
FIG. 1 is a flow chart diagram of one embodiment of a method for setting transmit power in medical diagnostic ultrasound imaging.

FIG. 1 shows a flowchart of a method for setting transmit power in medical diagnostic ultrasound imaging. The method is implemented by the system of FIG. 2, but a different system may be used. The transmit beamformer, receive beamformer, and image processor are configured in act 30 by the processor. The transmit beamformer and receive beamformer implement acts 34 and 36. A processor implements acts 32, 38, and 40. The imaging system provides for the imaging of act 42. Other systems for ultrasound scanning may be used. Other devices may implement one or more of the acts. The devices, as configured, operate in a new way to provide more efficient imaging. The acts improve the operation of the ultrasound imaging system.

Additional, different, or fewer acts may be provided. For example, other acts than acts 34-38 are performed to determine the harmonic-to-fundamental relationship of act 32. As another example, the transmit power is determined in act 40 without then imaging in act 42. In yet another example, one or more acts for receiving user input to configure the scanner in act 30 and/or to control (e.g., mapping selection) the automatic operation of the setting of transmit power are provided.

The acts are performed in the order shown or a different order. For example, the scanner is configured in act 30 after or as part of determining the power in act 40. As another example, acts 34 and 36 are performed in the order shown, a reverse order, or simultaneously.

In act 30, an ultrasound scanner is configured for imaging. The ultrasound scanner is a medical diagnostic ultrasound imaging system. In other embodiments, the ultrasound scanner is a therapy ultrasound system.

In response to user input, presets or a default, the ultrasound scanner is configured. The configuration may be for a particular application, such as fetal imaging. The configuration may be for a mode, such as B-mode or harmonic imaging. Alternatively, the user selecting one or more options manually arranges the configuration.

The configuration includes one or more settings. For beamforming, the settings may be a depth of the field of view, lateral extent of the field of view, scan format, line density, sample density, frequency of transmission, frequency of reception, pulse repetition frequency, and/or other settings. For detection, the settings may be the mode (e.g., B-mode, color flow mode, spectral Doppler mode, or M-mode), filtering (e.g., spatial and/or temporal), gain, depth gain, and/or other settings. Other configuration settings for any mode of ultrasound imaging may be provided.

In one embodiment, harmonic imaging is used. The ultrasound scanner is configured for harmonic imaging. The reception frequency is different than the transmit frequency. Any harmonic may be used, such as integer harmonics (e.g., second or third order harmonics of the fundamental frequency) or fractional harmonics (e.g., ½ or 1½ harmonic of the fundamental frequency). The fundamental frequency is the transmit frequency. For example, the fundamental frequency is 2 MHz. Transmitted pulses are generated with waveforms being at 2 MHz. For second order harmonic reception, the signals at 4 MHz are isolated or used. In alternative embodiments, fundamental frequency imaging is used. The transmit and receive frequencies are the same or within 5% of each other.

The discussion above is for center frequency. The ultrasound scanner operates in frequency bands of any bandwidth. Some of the fundamental band may be within the harmonic band. Alternatively, the fundamental and harmonic frequency bands of operation are separated by intensities at least 10 dB down.

The configuration may or may not include the tissue being scanned. By moving the transducer, the user arranges for particular tissue or region of the patient to be within the field of view. Since tissues acoustically respond in different ways, the configuration for a given imaging condition may include the placement of the scan region relative to the patient. Alternatively, the configuration does not include scan region positioning.

In act 32, a harmonic-to-fundamental relationship is calculated. A value that is a function of both harmonic and fundamental information is determined. Any method and metric may be used to determine the relationship. In the example of act 38, the relationship is a ratio. Additive, subtractive, multiplicative, divisional, combinations thereof, and/or other functions may be used. One or more values for each of fundamental and harmonic response to acoustic energy are combined to provide the value.

In the example discussed below, the ratio of harmonic and fundamental signals is used. A signal strength or intensity of harmonic response is divided by the signal strength or intensity of fundamental response, or vise versa. Acts 34-38 represent one embodiment for calculating the relationship. Additional, different, or fewer acts may be provided to calculate the relationship.

An ultrasound scanner measures the fundamental and harmonic responses in acts 34 and 36. The measurements are performed with the ultrasound scanner as configured for imaging after act 30. The field of view, line density, transmit frequency, and/or other settings are the same for measuring and imaging. One or more settings may be different for the measurements to set power, such as using a different type of harmonic imaging, different beamforming, and/or different detection. For example, the frequency and field of view are the same, but a sparse sampling for scanning with a lesser line density and/or sample density is used for measuring. As another example, the field of view is smaller for measuring. For harmonic imaging, the same harmonic frequency (e.g., 4 MHz) and harmonic order (e.g., $2^{nd}$ order) as the imaging harmonic frequency and order are used for measuring the harmonic response. Alternatively, a different harmonic frequency and/or order are used for measurement as compared to imaging.

The measurements of acts 34 and 36 are performed using detected data. The responses to transmission of acoustic energy are received at a transducer. The echoes are converted to electrical signals by the transducer. The receive beamformer generates beamformed samples as the received signal. Each sample represents different locations, such as along a scan line. The beamformed samples are detected by B-mode, color flow mode, spectral Doppler, M-mode or other process that converts the receive beamformed samples into a specific mode or determines a characteristic of the acoustic response. B-mode and M-mode detection are the intensity or power of the acoustic response. Color flow mode is the velocity, energy of motion, or variance estimation. Spectral Doppler is the frequency response of the motion. The detected signal used for measuring is before or after any of spatial filtering, temporal filtering, or scan conversion. In alternative embodiments, beamformed samples prior to detection are used for the measurements.

The measurements of acts 34 and 36 are performed for the response from a location. A given sample location is used. The samples representing that location are used to measure. Alternatively, the measurements are for a region, such as measuring an average response over a region including a plurality of sample locations. The fundamental and harmonic characteristics are determined for one or more spatial locations. Any size region may be used. The region is along one, two or three dimensions. For example, the transmit power is to be set for scanning performed along a single beam, such as associated with M-mode or Spectral Doppler imaging. The tissue responses at different sample locations along the beam are measured. For two or three-dimensional scanning, the response along all of the sample locations in the field of view as configured are measured. Alternatively, a lesser sample and/or line density is used. The field of view is sampled sparsely for the measurements. In another alternative, a smaller field of view is used with the same or different sample or line density as the field of view for imaging.

Since harmonic signals are higher frequency, the harmonic tends to attenuate more rapidly than the fundamental. In one embodiment, the region may be positioned at a deepest part of the field of view and/or region of interest so that sufficient power to provide harmonic information at the depth of interest is provided.

In act 34, a fundamental response is measured. The signal from the echoes at a fundamental or transmit frequency or frequency band is measured. The pulses to generate the acoustic energy and the resulting acoustic energy are at a transmit or fundamental frequency. The acoustic energy reflected back from tissue in the patient includes signal at the fundamental frequency. The transmission is performed at a frequency or frequency band, and the responsive signal at the same frequency or frequency band is measured.

In act 36, a harmonic response is measured. The signal from the echoes at a harmonic of the fundamental or transmit frequency or frequency band is measured. The acoustic energy reflected back from tissue in the patient includes signal at the harmonic frequency. The transmission is performed at a frequency or frequency band, and the responsive signal at a harmonic (e.g., second harmonic) of that fundamental frequency or frequency band is measured. The harmonic is a different frequency than the fundamental. As the transmitted acoustic energy and echo propagate, harmonic signal is generated. The reflection also generates harmonic signal. Different tissues and/or other substances (e.g., contrast agents) generate different amounts of harmonic signal.

For measuring, the signal at the desired frequency or frequency band may be isolated or partially isolated. For example, the signal is filtered by different filters or stored and sequentially filtered. The filter or filters reduce information at frequencies other than the desired harmonic or fundamental frequencies. In one filter or pass, primarily fundamental frequencies remain. In another pass or filter, primarily harmonic frequencies remain. Primarily is used to indicate a peak magnitude at least 5 dB greater for a frequency spectrum of the signal.

Other techniques to provide signal at the desired frequencies may be used. For example, a pulse inversion is used. The transmit beamformer generates two beams along a same scan line but with pulses at different phases. The pulses are generated in sequence, one at one phase and the other at another phase. The phase difference between the pulses of each transmission is shifted by 180 degrees. The beams or pluses are at a same magnitude. Alternatively, more than two pulses, different magnitudes, different amounts of phase separation, or combinations thereof may be used. The samples responsive to the different beams at a same location are added and subtracted. A memory or buffer delays the signal from the first transmission for adding by an adder and subtracting by a subtractor with the signal from the second or subsequent transmission. The summation of signals responsive to different phases passes information at a harmonic, such as the second order harmonic, and reduces information at the fundamental. The differencing of signals responsive to the different phases passes information at the fundamental, such as the transmit frequency, and reduces information at harmonics, such as the second harmonic.

In act 38, a ration of the fundamental and harmonic responses is calculated. The signal resulting from the harmonic measurement is divided by the signal represented by the fundamental measurement. Where signals are provided from different times or locations, the values for the signals may be averaged before calculating the ratio from the averages or multiple ratios are calculated and the ratios are averaged. Alternatively, the fundamental is divided by the harmonic.

In one embodiment, the ratio is of the second harmonic response to the fundamental frequency response of tissue of the patient. Other ratios and/or relationships may be used. The calculated relationship indicates the relative strength of the harmonic and fundamental components of the received signal.

Greater harmonic-to-fundamental ratio may result from greater transmit power. For harmonic imaging, a minimum ratio is desired but excess transmit power is undesired.

In act 40, the transmit power for an imaging condition is determined. Given the configured ultrasound scanner, an appropriate transmit power is set based on the relationship between fundamental and harmonic responses. The ultrasound scanner is configured with a field of view, frequency, and/or line density for scanning a patient. The fundamental-to-harmonic ratio for that configuration is used to set the transmit power.

To control transmit power, the amplitude of the transmit beamformer generated waveforms, the pulse repetition frequency, and/or the number of elements used in a transmit aperture is altered. For example, the transmit aperture and pulse repetition frequency remain as configured. The transmit amplitude is increased or decreased to provide more or less transmit power. The resulting acoustic energy has more or less power within the patient.

In one embodiment, the transmit power is set to have lesser powers for higher ratios of the harmonic response to the fundamental response. The higher ratio indicates excess power. A lower ratio indicates insufficient power. For ALARA, the goal is to provide sufficient power for imaging without excess power. By setting the transmit power based on the ratio or other relationship of relative strength, just sufficient harmonic imaging may be provided. The user may configure or set the mapping so that the user's perception of just sufficient is used. Alternatively, a pre-determined mapping of just sufficient is used.

The transmit power is set based on the ratio or other relationship of the fundamental and harmonic responses. In one embodiment, a curve or map relating the value of the relationship to the transmit power is used. The relationship value, such as the ratio, is used to look up a transmit power. Any map may be provided, such as a linear or non-linear mapping. The map is the same or different for different types of imaging, such as having a different map for fetal imaging than for cardiac imaging.

In another embodiment, a binary mapping is used. The relationship value is compared to a threshold. If the relationship is above the threshold, then one transmit power is used. Alternatively, the transmit power is increased or decreased by a given amount. If the relationship is below the threshold, then a different transmit power is used and/or the transmit power is decreased or increased by a given amount. More than one threshold may be used, such as having a range of no change in transmit power separating other ranges for higher and lower power.

In act 42, the patient is imaged by the ultrasound scanner. The ultrasound scanner operates or is configured with the set transmit power. The B-mode, color flow mode, or other mode of imaging the patient is performed. The transmissions for that imaging use the power determined in act 40.

Since the ultrasound scanner is configured for a particular imaging condition (e.g., particular settings) when the measurements for setting power are made, the power is set as appropriate for those imaging conditions. Since the power setting is responsive to scanning of the patient, the imaging conditions including the patient response in the field of view are accounted for in setting the power.

In one embodiment, the imaging being performed is fetal imaging. For fetal imaging, the harmonic response of tissue is, at least partially, isolated and detected. The resulting image, whether of a plane or volume (e.g., three-dimensional scanning) is of the harmonic response. Due to the measurement and setting of power, the harmonic response is more likely sufficient over the region of interest for clear or user sufficient imaging.

The imaging is performed as a function of the acoustic output power. Acoustic transmissions occur at the set power. The responsive echoes are detected and image processed in any desired manner. B-mode, color Doppler, velocity, variance, energy, M-mode, intensity, contrast agent, harmonic, tissue harmonic, flow, spectral Doppler, three-dimensional rendering, combinations thereof, or other now known or later developed imaging may be used.

In an alternative embodiment, the transmit power is set separately for different scan lines. Different measurements, relationship calculation, and power setting are performed for different scan lines or groups of scan lines. For example, the ratio is an average from along a range of deeper sample locations for a group of scan lines centered in the field of view. A separate ratio or ratios are calculated for scan lines at the edges of the field of view. The mapping is different for the different regions. Greater transmit power is used or set for the center regions than for the edge regions.

A feedback is shown from act 42 to the configuration of act 30. This feedback represents altering the configuration with the transmit power, and then repeating the calculation of the relationship in act 32 and the power determination in act 40. This repetition may be part of an iterative process to set the transmit power. Based on the imaging condition, an optimal transmit power is found. The power is determined with incremental changes (e.g., increase or decrease power by an amount based on the relationship) to find a transmit power providing the desired relationship. In other embodiments, feedback is not used.

In another embodiment, the feedback represents altering the configuration with a change to other settings than the transmit power and/or with a change in other imaging conditions. For example, the user alters the field of view or other setting. As another example, the user repositions the transducer so that a different region of the patient is being scanned. The ultrasound scanner detects the change or alteration and repeats the measuring of the fundamental and harmonic responses, calculating, and setting of the transmit power in response to the altering. The user may trigger repetition, such as by depressing a button.

Figure 2:
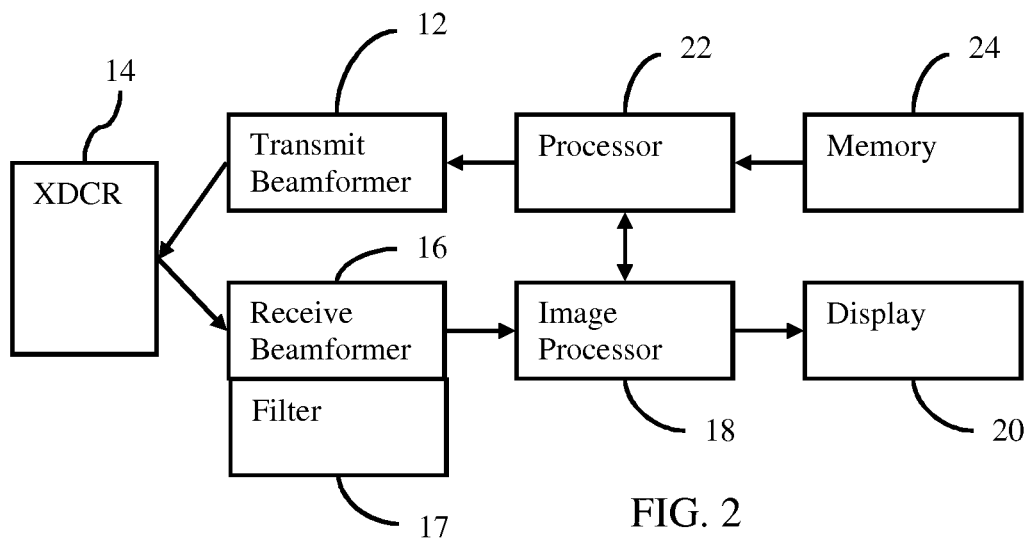
FIG. 2 is a block diagram of an embodiment of an ultrasound system for setting transmit power.

FIG. 2 shows one embodiment of a medical diagnostic imaging system 10 for setting transmit power. The system 10 implements the method of FIG. 1 or other methods. The system 10 includes a transmit beamformer 12, a transducer 14, a receive beamformer 16, a filter 17, an image processor 18, a display 20, a processor 22, and a memory 24. Additional, different or fewer components may be provided. For example, a user input is provided for manual or semi-automated indication of a region of interest and/or triggering setting of the power. As another example, the processor 22 is part of one of the other components, such as a beamformer controller or the image processor 18.

The transmit beamformer 12 is an ultrasound transmitter, memory, pulser, analog circuit, digital circuit, or combinations thereof. The transmit beamformer 12 includes waveform generators and is operable to generate waveforms for a plurality of channels with different or relative amplitudes, delays, and/or phasing. The transmit beamformer 12 includes one or more amplifiers for setting the amplitude of the waveforms. Alternatively, the waveform generators set the amplitude. The transmit beamformer 12 includes one or more phase shifters or delays for setting a phase of the waveforms. Alternatively, the waveform generators establish the phase.

Upon transmission of acoustic waves from the transducer 14 in response to the generated waves, one or more beams are formed. A sequence of transmit beams are generated to scan a two or three-dimensional region. Sector, Vector®, linear, or other scan formats may be used. The same region is scanned one time or multiple times. For flow or Doppler imaging and for strain imaging, a sequence of scans to a same region is used. In Doppler imaging and shear velocity estimation, the sequence may include multiple beams along a same scan line before scanning an adjacent scan line. For strain or elasticity imaging, scan or frame interleaving may be used (i.e., scan the entire region before scanning again). In alternative embodiments, the transmit beamformer 12 generates a plane wave or diverging wave for more rapid scanning.

The transmit beams are formed at different energy or amplitude levels. Amplifiers for each channel and/or aperture size control the amplitude of the transmitted beam. The transmit beams are formed with a given phase. The waveforms for the channels or elements have a phase. The transmit beamformer 12 may shift the phases for different transmissions, such as generating two beams along a same scan line in sequence where one beam is 180 degrees out of phase with the other beam. The waveforms for generating one beam are out of phase with the waveforms for generating the other beam relative to the initiation of the respective transmission. Other characteristics may be adjusted, such as the pulse repetition frequency or frequency of the waveforms.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. The elements connect with channels of the transmit and receive beamformers 12, 16.

Under the control of the processor 22, the transmit beamformer 12 causes the transducer 14 to transmit acoustic energy. The transmission is along one or more scan lines. The acoustic energy has a power controlled by the transmit beamformer 12, such as by setting the amplitude and/or aperture size of the waveforms applied to the transducer 14. Acoustic echoes responsive to the transmission are received by the transducer 14. The transducer 14 receives these responses at the elements and transduces the acoustic responses into electrical energy. Receive signals are generated in response to ultrasound energy (echoes) impinging on the elements of the transducer 14.

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to a transmission. In alternative embodiments, the receive beamformer 16 is a processor for generating samples using Fourier or other transforms.

The receive beamformer 16 may include the filter 17, such as a filter for isolating information at a second harmonic, fundamental or other frequency band relative to the transmit frequency band. Multiple filters for isolating at different frequency bands may be used, or a programmable filter sequentially isolates. In alternative embodiments, the filter 17 is not provided, is separate from the receive beamformer 16, and/or is part of the image processor 18 or the processor 22.

In another embodiment, the receive beamformer 16 includes a memory or buffer and a filter or adder. Two or more receive beams are combined to isolate information at a desired frequency band, such as a second harmonic, cubic fundamental or other band. For example, the receive beamformer 16 sums beamformed signals responsive to transmission 180 degrees out of phase with each other to provide harmonic signal and subtracts the same signals to provide fundamental signal.

The receive beamformer 16 outputs beam summed data representing spatial locations. Data for a single location, locations along a line, locations for an area, or locations for a volume are output. Dynamic focusing may be provided. The data may be for different purposes. For example, different scans are performed for B-mode or tissue data than for measuring to set the transmit power. The receive beamformer 16 may include one or more amplifiers for altering a gain of the received signals.

The image processor 18 is a B-mode detector, Doppler detector, pulsed wave Doppler detector, correlation processor, Fourier transform processor, or other processor or circuit for detecting from beamformed ultrasound samples and processing information for display. In one embodiment, the processor 18 includes one or more detectors and a separate processor. The image processor 18 detects data from the beamformed samples and generates a medical diagnostic ultrasound image. The image processor 18 or other devices may implement filtering, scan conversion, rendering, or other processes.

The processor 22 is an application specific integrated circuit, beamformer controller, general processor, control processor, image processor, field programmable gate array, digital signal processor, analog circuit, digital circuit, network, server, group of processors, combinations thereof, or other now known or later developed device for determining a transmit power value and controlling the transmit beamformer 12 based on the transmit power value. The processor 22 may be a single device or combinations of devices. The processor 22 may be the image processor 18 or is a separate device or devices. The processor 22 is configured by software, hardware, and/or firmware to determine a relationship between harmonic and fundamental signals and to set a transmit power based on the relationship.

The processor 22 uses receive signals from the image processor 18 and/or the receive beamformer 16 to determine a relationship between harmonic and fundamental signals. The signals are detected data, non-detected receive beamformed data, or non-receive beamformed channel data. In other embodiments, the processor 22 receives input from other sources, such as other systems configured to calculate the relationship.

The processor 22 is configured to determine the relationship using any function. Two variables of the function are the harmonic signal and the fundamental signal. Other variables may be used. Any combination of values from variables may be used. In one embodiment, the processor 22 calculates a ratio of the harmonic signal to the fundamental signal. The value of the harmonic signal is divided by the value of the fundamental signal. The values may be responses from tissue in one location or average responses from tissue in multiple sample locations. Ratios may be calculated for multiple locations and averaged, summed, or combined.

The processor 22 is configured to set a power of subsequent transmission of acoustic energy as a function of the relationship. The relationship is mapped to a transmit power using a look-up (e.g., look-up table) or by function calculation. Different values of the relationship, such as the ratio, result in different transmit powers. Different values of the relationship may map to the same transmit power. Any linear or non-linear mapping may be used. In other embodiments, the process is iterative. The relationship is used to increase or decrease the transmit power by a given amount based on comparison to a threshold or thresholds. If not enough relative strength of harmonic, the power is increased. If there is excess relative strength in the harmonic signal, then the power is decreased. The measurement is performed again with the altered power. Once the relationship is within a desired range, the resulting transmit power is used for imaging. In other embodiments, the relationship is compared to a threshold. If on one side of the threshold (e.g., greater than), then one transmit power setting is used for imaging. If on another side of the threshold (e.g., less than), then a different transmit power setting is used for imaging. Other settings of the transmit power based on the relationship may be used.

The transmit power is set to provide sufficient harmonic or other mode of imaging, but while avoiding use of excess power. The thresholds or mapping may implement the ALARA principle, such as for fetal imaging, without errors in harmonic imaging caused by SNR-based power setting. In other embodiments, ALARA is not implemented, but the power is mapped using different principles. In yet other embodiments, additional information is used to set the power, such as also measuring SNR and using SNR to determine, in part, the transmit power.

The setting of the transmit power is applied to the transmit beamformer 12. For transmissions by the transmit beamformer 12 after the value of the setting is determined, the set transmit power is used. The transmit power setting is used for imaging the patient, such as scanning and generating an image representing the scanned region in a harmonic imaging mode.

The processor 22 operates pursuant to instructions stored in the memory 24 or another memory. The processor 22 is programmed for setting transmit power in medical diagnostic ultrasound imaging. The memory 24 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display device 20 is a CRT, LCD, projector, plasma, printer, or other display for displaying ultrasound images, graphics, and/or a user interface. The ultrasound images are two-dimensional images. Alternatively or additionally, a three-dimensional rendering to the two-dimensional display 20 is provided. The image represents the acoustic response of the patient to ultrasound scanning using the set transmit power. In one embodiment, harmonic images are shown, but other imaging modes may be used. The display device 20 outputs an image of a region of the patient, such as a two-dimensional elasticity, Doppler tissue, color Doppler, flow, spectral Doppler, M-mode, harmonic, contrast agent, acoustic force radiation, elasticity, strain, shear, or B-mode image.

The foregoing detailed description has been intended by way of illustration and not limitation. It is only the following claims, including all equivalents, that are intended to define the scope of this invention.

The invention claimed is:

1. A method for setting transmit power in medical diagnostic ultrasound imaging to ensure patient safety, the method comprising:

measuring, with an ultrasound scanner, a fundamental response of tissue at a location in a patient, the location being selected to be at a deepest location of a field of view or region of interest in the patient;

measuring, with the ultrasound scanner, a harmonic response at the location;

calculating a ratio of the fundamental and harmonic responses from the location at the deepest location of the field of view or the region of interest;

setting a transmit power of a transmitter of the ultrasound scanner as a function of the ratio of the fundamental and harmonic responses such that harmonic information for imaging the tissue is provided for the field of view or region of interest; and imaging the tissue with the harmonic information in the field of view or region of interest in the patient with the ultrasound scanner using the transmit power.

2. The method of claim 1 wherein measuring the fundamental response comprises transmitting at a first frequency band and receiving at the first frequency band, and wherein measuring the harmonic response comprises transmitting at the first frequency band and receiving at a second frequency band different than the first frequency band.

3. The method of claim 1 wherein measuring the harmonic response comprises measuring a second harmonic to a fundamental frequency.

4. The method of claim 1 wherein measuring the fundamental and harmonic responses comprises:
transmitting first and second pulses having phases differing by 180 degrees;
adding first and second responses to the first and second pulses, respectively, for the harmonic response; and
subtracting the first and second responses for the fundamental response.

5. The method of claim 1 wherein measuring the fundamental and harmonic responses comprises measuring from detected data.

6. The method of claim 1 wherein measuring the fundamental and harmonic responses comprises measuring average responses in an area having multiple locations including the location, the area being at the deepest location of the field of view or the region of interest.

7. The method of claim 1 further comprising:
configuring the ultrasound scanner for the imaging, the configuring including setting of the field of view, a line density, and a frequency and being performed prior to the measuring of the fundamental and harmonic responses;
wherein measuring the fundamental and harmonic responses comprises measuring with the settings of the field of view, line density, and frequency.

8. The method of claim 7 further comprising:
altering the configuring; and
repeating the measuring of the fundamental and harmonic responses, calculating, and setting of the transmit power in response to the altering.

9. The method of claim 1 wherein calculating the ratio comprises dividing the harmonic response by the fundamental response.

10. The method of claim 1 wherein setting comprises setting with the transmit power mapped to lesser powers for higher ratios of the harmonic response to the fundamental response.

11. The method of claim 1 wherein setting comprises setting an amplitude, a number of elements, or the amplitude and the number of elements.

12. The method of claim 1 wherein setting comprises comparing the ratio to a threshold value and selecting the transmit power as a first level with the ratio below the threshold value and selecting the transmit power as a second level with the ratio above the threshold value in a binary mapping.

13. The method of claim 1 wherein the imaging comprises harmonic imaging.

14. The method of claim 13 wherein measuring the harmonic response comprises measuring at a harmonic used in the imaging.

* * * * *